United States Patent
Fry et al.

(10) Patent No.: US 8,306,265 B2
(45) Date of Patent: Nov. 6, 2012

(54) DETECTION OF ANIMATE OR INANIMATE OBJECTS

(75) Inventors: Peter T. Fry, Wicken (GB); Andrew F. Kurtz, Macedon, NY (US)

(73) Assignee: Eastman Kodak Company, Rochester, NY (US)

( * ) Notice: Subject to any disclaimer, the term of this patent is extended or adjusted under 35 U.S.C. 154(b) by 843 days.

(21) Appl. No.: 12/406,186

(22) Filed: Mar. 18, 2009

(65) Prior Publication Data

US 2010/0177968 A1  Jul. 15, 2010

Related U.S. Application Data

(60) Provisional application No. 61/143,940, filed on Jan. 12, 2009, provisional application No. 61/144,214, filed on Jan. 13, 2009.

(51) Int. Cl.
*G06K 9/00* (2006.01)
(52) U.S. Cl. ......... 382/103; 382/224; 348/143; 348/169
(58) Field of Classification Search .................. 382/103, 382/224; 348/143, 169
See application file for complete search history.

(56) References Cited

U.S. PATENT DOCUMENTS

| | | | |
|---|---|---|---|
| 6,807,438 B1 | 10/2004 | Brun Del Re et al. | |
| 7,043,075 B2 * | 5/2006 | Gutta | 382/158 |
| 7,078,911 B2 | 7/2006 | Cehelnik | |
| 7,831,100 B2 * | 11/2010 | Gallagher | 382/224 |
| 2003/0169339 A1 * | 9/2003 | Allen et al. | 348/169 |
| 2005/0201612 A1 | 9/2005 | Park et al. | |
| 2006/0056655 A1 * | 3/2006 | Wen et al. | 382/103 |
| 2006/0058694 A1 | 3/2006 | Clark et al. | |
| 2008/0239076 A1 | 10/2008 | Luo | |
| 2009/0024017 A1 | 1/2009 | Ruffini et al. | |
| 2009/0069642 A1 * | 3/2009 | Gao et al. | 600/300 |
| 2010/0316253 A1 * | 12/2010 | Yang et al. | 382/103 |

FOREIGN PATENT DOCUMENTS

| | | |
|---|---|---|
| GB | 0710132.2 | 5/2007 |
| WO | 2007/088328 | 8/2007 |
| WO | 2007/107689 | 9/2007 |
| WO | 2008/009906 | 1/2008 |
| WO | 2008/145957 | 12/2008 |

OTHER PUBLICATIONS

Harland et al., "Non-invasive Human Body Electrophysiological Measurements using Displacement Current Sensors", 2004, Body Sensor Networks Workshop Program Universidade de Sussex, vol. 73, Issue: 3.*

A. L. Yuille, et al., "Feature extraction from faces using deformable templates", International Journal of Computer Vision, vol. 8, 1992, pp. 104-109.

(Continued)

*Primary Examiner* — Jason M Repko
*Assistant Examiner* — Katrina Fujita
(74) *Attorney, Agent, or Firm* — Raymond L. Owens (57) ABSTRACT

Image data representing a captured image of an environment or a portion thereof, and electric-field data representing electric fields present in the environment or a portion thereof are received. The electric-field data and the image data represent information gathered from an overlapping portion of the environment. A candidate object is identified in the overlapping portion and classified as animate or inanimate based at least upon an analysis of the image data and the electric-field data.

27 Claims, 6 Drawing Sheets

OTHER PUBLICATIONS

S. Cotton, et al., Developing a predictive model of human skin colouring, Proceedings of SPIE, vol. 2708, 1996, pp. 814-825.

D. A. Forsyth, et al., "Finding People and Animals by Guided Assembly", Conference on Image Processing, vol. 3, 1997.

R. J. Prance, et al., "An ultra-low-noise electrical-potential probe for human-body scanning", Meas. Sci. Technol. 11, 2000, pp. 291-297.

C. J. Harland, et al., "Remote detection of human electroencephalograms using ultrahigh input impedance electric potential sensors", Applied Physics Letters, vol. 81, No. 17, 2002, pp. 3284-3286.

J. Harland, et al., "Electric potential probes—new directions in the remote sensing of the human body", Meas. Sci. Technol. 13, 2002, pp. 163-169.

J. B. Dowdall, et al., "Face Detection in the Near-IR Spectrum", Proc. SPIE, vol. 5074, 2003, pp. 745-756.

R. L. Hamlin, "Non-drug-related electrocardiographic features in animal models in safety pharmacology", Journal of Pharmacological and Toxicological Methods, vol. 52, 2005, pp. 60-76.

D. Hoiem, et al., "Putting Objects in Perspective", IEEE Proc. on Computer Vision and Pattern Recognition (CVPR), 2006.

Y. Yacoob, et al., "Detection, Analysis and Matching of Hair", IEEE Trans. on PAMI, vol. 28, 2006.

R. J. Prance, et al., "Biological and medical applications of a new electric field sensor", Proc. ESA Annual Meeting on Electrostatics, 2008, paper N2.

\* cited by examiner

DETECTION OF ANIMATE OR INANIMATE OBJECTS

CROSS-REFERENCE TO RELATED APPLICATION(S)

This application claims the benefit of U.S. Provisional Application Ser. No. 61/143,940 filed Jan. 12, 2009, and claims the benefit of U.S. Provisional Application Ser. No. 61/144,214 filed Jan. 13, 2009, each of which is incorporated herein by reference in its entirety.

This application is related to commonly assigned U.S. patent application Ser. No. 12/352,030, filed Jan. 12, 2009, and titled "Enhanced Safety During Laser Projection," by Kurtz et al.

FIELD OF THE INVENTION

Embodiments of the present invention relate to, among other things, detecting animate or living objects. In some embodiments, candidate objects within an environment are detected by a combination of bio-electric field sensors and cameras, and then classified appropriately, including as animate or inanimate.

BACKGROUND

Common everyday environments are populated with both animate (living) and inanimate (non-living) objects. Under most conditions, both people and animals can view such an environment and quickly distinguish animate and inanimate objects from each other. A variety of cues, including object recognition, motion, audio, and social context are used in these assessments.

By comparison, the technological equivalent, for example, real-time automated sensing systems relying on cameras and microphones, and appropriate interpretive programs and databases are neither as efficient nor versatile as a human at this type of task. Additionally, there are complicating circumstances which can make the sensing and classification task much more difficult, particularly for an automated system, and on occasion, even for people. For example, some inanimate objects (such as stuffed animals or card-board cut-outs of people) can be particularly difficult to detect correctly as inanimate, depending on the time and other cues available. Likewise, hidden or obscured objects (people or animals in difficult poses or clothing (towel over their head)), stationary people, or projected images of people can be particularly difficult, unreliable, or time consuming, for imaging techniques (including face detection, body shape detection, motion detection) alone to correctly distinguish animate and inanimate objects from one another.

Accordingly, a need in the art exists for improved techniques for detecting and classifying animate (living) or inanimate (non-living) objects.

SUMMARY

The above-described problems are addressed and a technical solution is achieved in the art by systems and methods for detecting objects in an environment, according to various embodiments of the present invention. In an embodiment of the present invention, image data is received representing a captured image of the environment or a portion thereof. Electric-field data from or derived from an electric field sensing system also is received, the electric-field data representing electric fields present in the environment or a portion thereof, and the electric-field data and the image data representing information gathered from an overlapping portion of the environment. A candidate object is detected in the overlapping portion of the environment and classified as animate or inanimate, based at least upon an analysis of the image data and the electric-field data. The analysis of the electric-field data includes an evaluation of whether the electric-field data represents a bio-electric field. Information pertaining to results of the classifying is stored in a processor-accessible memory system. A responsive device can be instructed to take action based at least upon the results. By identifying and classifying a candidate object based at least upon an analysis of both the image data and the electric-field data, more reliably results can be achieved over conventional techniques that rely on analyses of image data or electric-field data alone.

In some embodiments, the detecting, the classifying, or both of the candidate object includes analyzing the image data using body shape detection, head detection, skin area detection, face detection, eye detection, motion analysis, combinations thereof. Eye detection, and more specifically, in some embodiments, eye detection using eye-specific deformable templates or pet-eye detection can be used.

In some embodiments, if the candidate object is classified as animate, the candidate object is further classified as human or animal. If the candidate object is classified as animal, the candidate object can be further classified as a particular type of animal.

In some embodiments, the electric-field data includes heart beat activity information associated with the candidate object. The heart beat activity information can be analyzed in an attempt to classify an animate object as human or animal. The heart beat activity information can represent an electrocardiogram (ECG). In some embodiments, the heart beat activity information can include heart beat frequency, pulse shape, or timing, and the analysis of the heart beat activity information includes an analysis of the heart beat frequency, pulse shape, or timing.

In some embodiments, the electric-field data includes electro-encephalogram (EEG) information or electro-oculogram (EOG) information associated with the candidate object.

In some embodiments, the electric-field data includes ambient electric field information representing ambient electric fields present in the environment. In these cases, the candidate object can be classified as an inanimate moving object based at least upon an analysis of spatio-temporal changes in electric fields derived at least in part from the ambient electric field information. In some embodiments, the candidate object is classified as inanimate based at least upon a detecting of differential electric fields represented in the electric-field data.

In some embodiments, the classifying of the candidate object can include calculation of confidence values indicating a probability that the candidate object correctly matches a determined classification.

In situations where the classifying of an object as animate or inanimate is indeterminate or indicative of an uncertain classification, then continued detecting and classifying activities related to that object can occur.

In addition to the embodiments described above, further embodiments will become apparent by reference to the drawings and by study of the following detailed description.

BRIEF DESCRIPTION OF THE DRAWINGS

The present invention will be more readily understood from the detailed description of exemplary embodiments presented below considered in conjunction with the attached drawings, of which.

It is to be understood that the attached drawings are for purposes of illustrating the concepts of the invention and may not be to scale.

DETAILED DESCRIPTION

Various embodiments of the present invention pertain to determining whether an object in an environment or field-of-view is animate (e.g., living) or inanimate (non-living) by analyzing image data captured from a camera system and electric-field data captured from an electric-field sensing system. Some embodiments go further and classify the type of animate object (e.g., human animal) detected, if the object is deemed animate. Image data is suited for, among other things, detecting objects, determining their locations and boundaries, and for further classifying objects by type, once they are deemed animate or inanimate. However, image data cannot readily detect or classify hidden, obscured, or confusing objects. Electric-field data, and particularly bio-electric field data is suited for directly detecting the presence and location of animate objects while ignoring the presence of many inanimate objects that can confuse imaging approaches. Bio-electric field sensing also is useful for classifying detected objects as animate, even when they are obscured. However, electric-field data, and bio-electric field data in particular, is less suited for general object detection, such as detecting inanimate (non-living) objects or object boundaries. Electric field sensing is particularly ill suited for detecting passive inanimate objects that do not emit electric fields of their own. Consequently, it has been determined that the combination of image data and electric-field data improves object detection and classification.

The invention is inclusive of combinations of the embodiments described herein. References to "a particular embodiment" and the like refer to features that are present in at least one embodiment of the invention. Separate references to "an embodiment" or "particular embodiments" or the like do not necessarily refer to the same embodiment or embodiments; however, such embodiments are not mutually exclusive, unless so indicated or as are readily apparent to one of skill in the art. The use of singular and/or plural in referring to the "method" or "methods" and the like is not limiting.

It should be noted that, unless otherwise explicitly noted or required by context, the word "or" is used in this disclosure in a non-exclusive sense.

Figure 2:
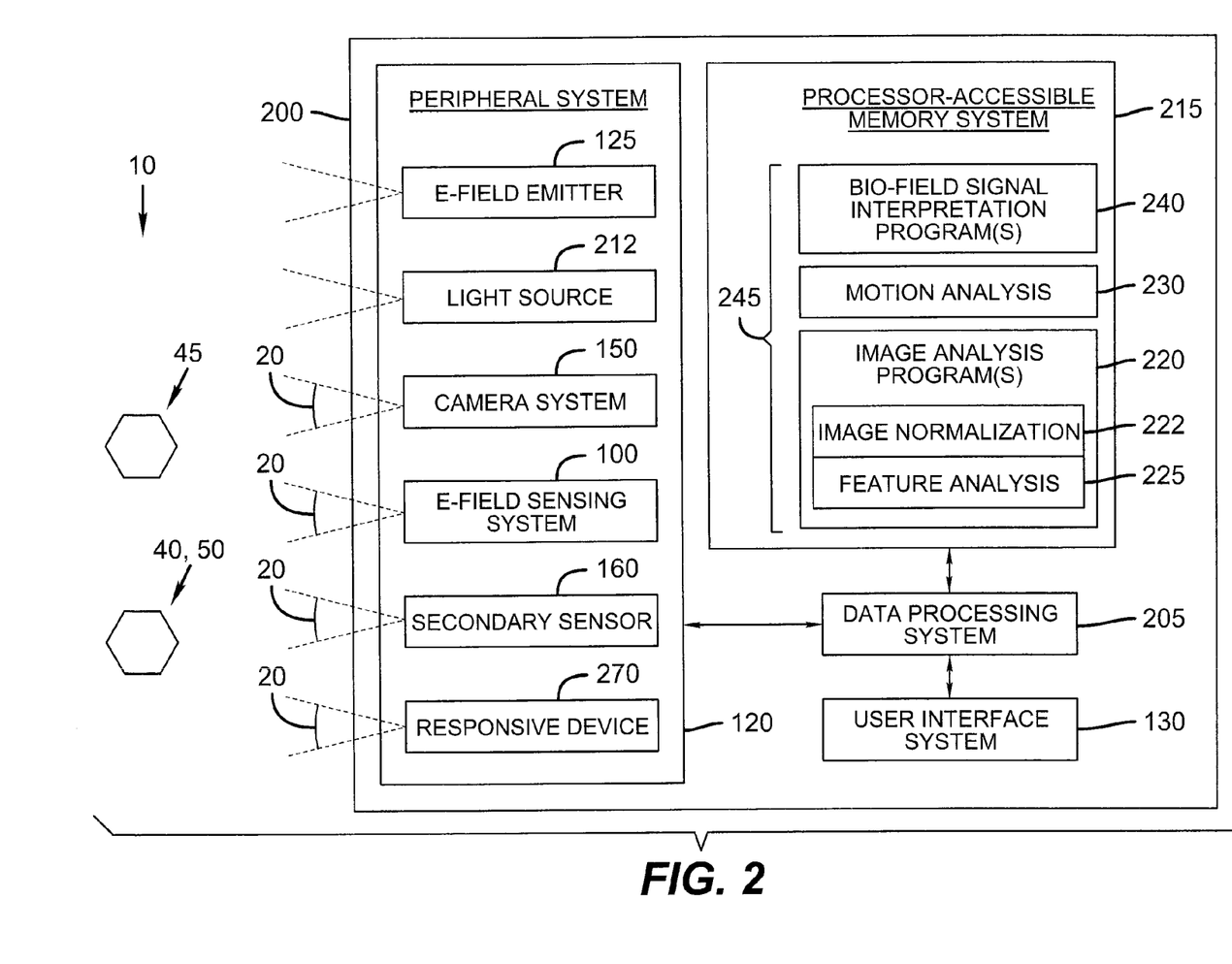
FIG. 2 illustrates a system, in which one or more electric field sensors and cameras are used to detect animate or inanimate objects, according to an embodiment of the present invention.

FIG. 2 illustrates a system 200 for detecting objects 45, and particularly animate objects (50) or inanimate objects (40) within a local environment 10, according to an embodiment of the present invention. The system 200 includes a data processing system 205, a peripheral system 120, a user interface system 130, and a processor-accessible memory system 215. The processor-accessible memory system 215, the peripheral system 120, and the user interface system 130 are communicatively connected to the data processing system 205.

Figure 3:
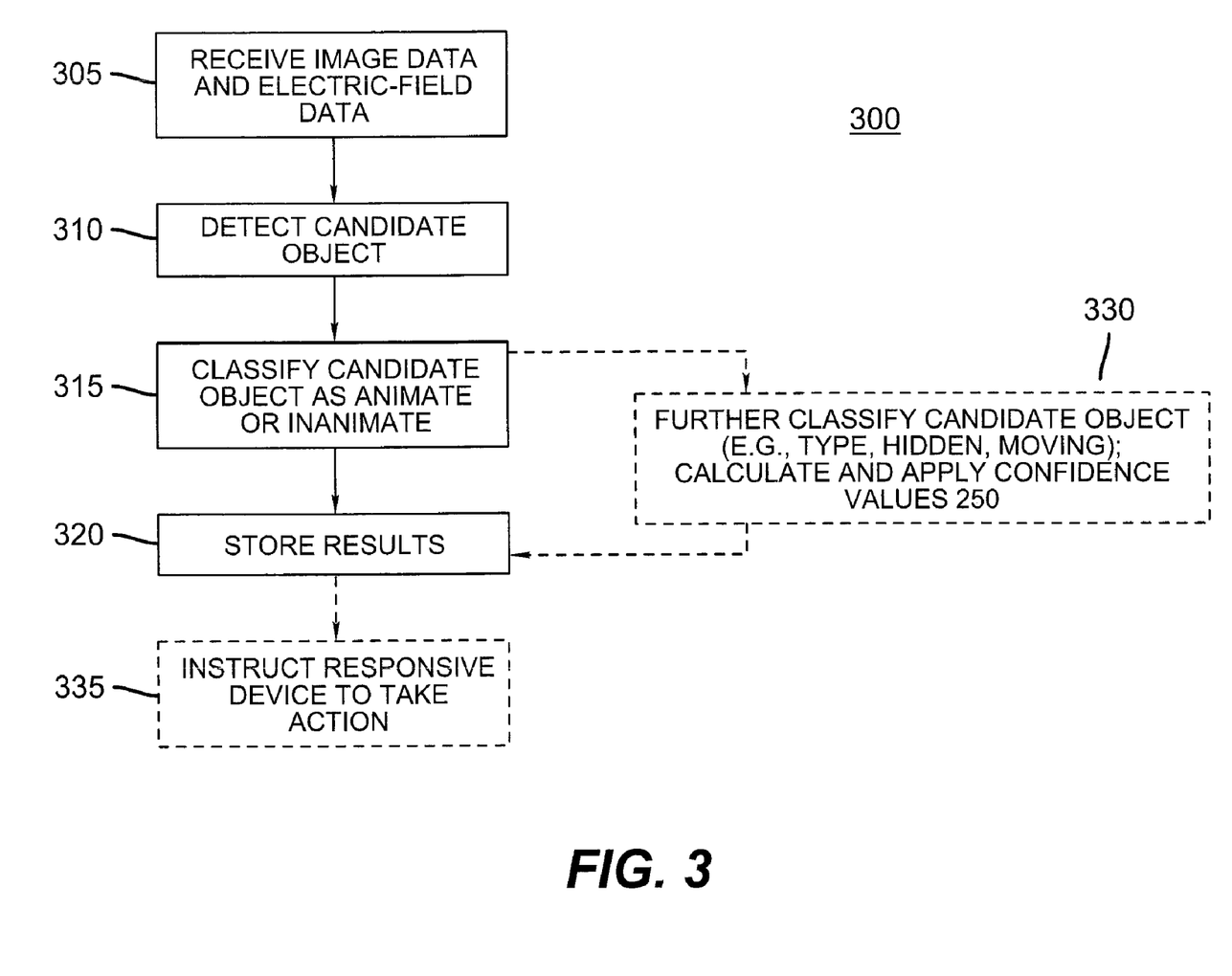
FIG. 3 illustrates a method, by which one or more electric field sensors and cameras are used to detect animate or inanimate objects, according to an embodiment of the present invention.

The data processing system 205 includes one or more data processing devices that implement the processes of the various embodiments of the present invention, including, for example, the processes of FIG. 3 described herein. The phrases "data processing device" or "data processor" are intended to include any data processing device, such as a central processing unit ("CPU"), a desktop computer, a laptop computer, a mainframe computer, a personal digital assistant, a Blackberry™, a digital camera, cellular phone, or any other device for processing data, managing data, or handling data, whether implemented with electrical, magnetic, optical, biological components, or otherwise.

The processor-accessible memory system 215 of FIG. 2 includes one or more processor-accessible memories configured to store information, including the information needed to execute the processes of the various embodiments of the present invention, including, for example, the processes of FIG. 3 described herein. In this regard, the data processing system 215 of FIG. 2 stores several environmental data interpretation programs 245, such as bio-electric field signal interpretation programs 240, motion analysis programs 230, and image analysis programs 220. The term "program," as used herein, is intended to refer at least to an implementation of an algorithm that controls or is configured to control the data processing system 205. The image analysis programs can include feature analysis programs 225 and optional image normalization programs 222, as described in more detail below. The motion analysis programs 230 can include image based or non-image based programs for analyzing input data to sense or classify moving objects. In some embodiments, the programs in memory system 215 include artificial intelligence (AI), e.g., a set of programs that can adaptively respond or anticipate object classifications or movement. The data processing system 205 can also optimize its performance to a given local environment 10, for example by having an intelligent agent that is also a learning system. For example, as a learning system, the system 200 can retain, analyze and classify data related to the local environment 10 in which it operates, to determine attributes related to the environment itself or objects therein. This acquired knowledge can be used as a basis for subsequent system operation, potentially enhancing the speed or accuracy of system operation.

The processor-accessible memory system 215 of FIG. 2 can be a distributed processor-accessible memory system including multiple processor-accessible memories communicatively connected to the data processing system 205 via a plurality of computers, devices, or both. On the other hand, the processor-accessible memory system 215 need not be a distributed processor-accessible memory system and, consequently, can include one or more processor-accessible memories located within a single data processor or device.

The phrase "processor-accessible memory" is intended to include any processor-accessible data storage device, whether volatile or nonvolatile, electronic, magnetic, optical, or otherwise, including but not limited to registers, floppy disks, hard disks, Compact Discs, DVDs, flash memories, ROMs, and RAMs.

The phrase "communicatively connected" is intended to include any type of connection, whether wired or wireless, between devices, data processors, or programs in which data can be communicated. Further, the phrase "communicatively connected" is intended to include a connection between devices or programs within a single data processor, a connection between devices or programs located in different data processors, and a connection between devices not located in data processors at all. In this regard, although the processor-accessible memory system 215 is shown separately from the data processing system 205, one skilled in the art will appreciate that the processor-accessible memory system 215 can be stored completely or partially within the data processing system 205. Further in this regard, although the peripheral system 120 and the user interface system 130 are shown separately from the data processing system 205, one skilled in the art will appreciate that one or both of such systems can be stored completely or partially within the data processing system 205.

Figure 1:
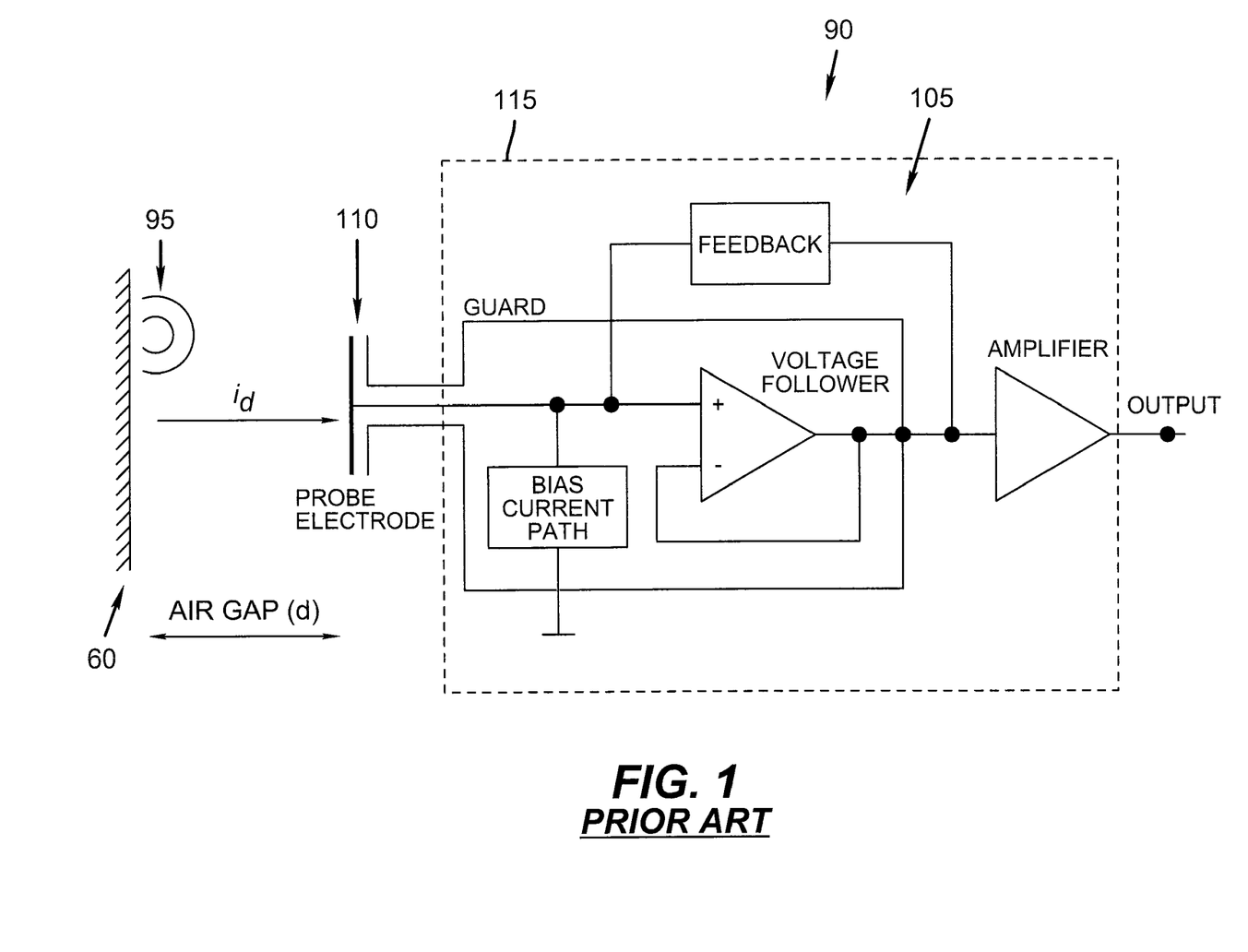
FIG. 1 illustrates one example of a prior-art bio-electric field sensor usable with the present invention.

The peripheral system 120 of FIG. 2 can include one or more devices configured to provide of facilitate the provision of data to the data processing system 205. The peripheral system 120 includes a video or still image camera system 150 and an electric field sensing system 100. The camera system 150 includes one or more video or still image cameras, and the electric field sensing system 100 includes one or more electric field sensors capable of detecting bio-electric fields. Both the camera system 150 and the electric field sensing system 100 are used in detecting and classifying objects 45, and animate objects 50 or inanimate objects 40. A bio-electric field sensor 90 usable in electric field sensing system is depicted in FIG. 1 and described in more detail below.

It should be noted that the present invention is not limited to the type of camera(s) used in camera system 150. For example, the camera system 150 may include visible or infrared (IR) light cameras, IR thermal cameras, or both. Camera(s) 150 can have a fixed focus lens (including hyperfocal), a fish eye lens (with a field of view, short focal distance, but much distortion), or a zoom lens. Multiple cameras, or stereo capture cameras, can also be used. The cameras 150 can also be panned and tilted to aid area monitoring, and either still or video can be acquired.

The peripheral system 120 can also include other devices, including a reference electric field emitter 125, a light source 212, other secondary sensors 160, or other data processors. Electric field emitter 125, in some embodiments, can be an electric field emission system including a plurality of electric field emitters. Regardless, each electric field emitter emits known electric fields into the environment 10, the emitted electric fields interacting with objects in the environment 10 and providing return electrical fields sensed by the electric-field-sensing system 100. Secondary sensors can provide secondary sensing data representing audio information, microwave information, ultrasound information, or combinations thereof, present in the environment. Such secondary sensing data can be used by the data processing system 205 to further facilitate detecting and classifying of objects in the environment 10.

The data processing system 205 of FIG. 2, upon receipt of data from a device in the peripheral system 120, can store such data in the processor-accessible memory system 215. For example, the data processing system 150 can receive image data from the camera 150 and electric-field data from the bio-electric field sensors 90 and store such data in the processor-accessible memory system 215.

The peripheral system 120 can include one or more devices to which data is output by the data processing system 205, such as other data processors or processor-accessible memories. In this regard, for example, the peripheral system 120 can include a responsive device 270 configured to be controlled by the data processing system 205. For example, the data processing system 205 may control the responsive device 270 to take action depending upon whether an animate or inanimate object is detected.

The user interface system 130 of FIG. 2 can include a mouse, a keyboard, another computer, or any device or combination of devices from which data is input to the data processing system 205. In this regard, although the peripheral system 120 is shown separately from the user interface system 130, the peripheral system 120 can be included as part of the user interface system 130, or vice versa.

The user interface system 130 also can include a display device, a processor-accessible memory, or any device or combination of devices to which data is output by the data processing system 205. In this regard, if the user interface system 130 includes a processor-accessible memory, such memory can be part of the processor-accessible memory system 215 even though the user interface system 130 and the processor-accessible memory system 215 are shown separately in FIG. 2.

In the peripheral system 120, the camera system 150 acquires image data representing a captured image of an environment 10 or a portion thereof. The electric field sensing system 100 acquires electric-field data representing electric fields present in the environment 10 or a portion thereof. The image data and the electric-field data represent information gathered from an overlapping portion of the environment 10. In a configuration where the camera system 150 includes multiple cameras, each camera can image a different field-of-view 20. These different fields-of-view (FOV) can be combined to form an image map of the environment 10 or a portion thereof. Similarly, in a configuration where the bio-field sensing system 100 includes multiple sensors, each electric field sensor can detect fields from a different field-of-view 20. These different fields-of-view can be combined to form a bio-electric field map of the environment 10 or a portion thereof. Regardless of whether the camera system 150 includes more than one camera, and regardless of whether the electric field sensing system 100 includes more than one sensor 90, the region of the environment 10 represented by image data acquired by the camera system 150 overlaps the region of the environment 10 represented by the electric-field data acquired by the electric field sensing system. In this overlapping portion or combined FOV 20, the data processing system 205 determines whether a sensed object 45 (in FIG. 2, for example) is present, and whether it is animate or inanimate based at least upon an analysis of the image data and the electric-field data it receives from the camera system 150 and the electric field sensing system 100, respectively.

In some embodiments of the present invention, a two-dimensional or three-dimensional map of the overlapping portion of the environment 10 can be generated by combining the image map (from the image data from camera system 150) and the bio-electric field map (from the electric-field data from the electric field sensing system 100). A three dimensional map can be useful in representing where object are located in space within n environment 10, or in tracking their motion through that space (or FOV). Relative to mapping, it is useful to locate at least one camera in camera system 150 and at least one bio-field sensor in sensing system 100 can be positioned in close proximity, such that the environment 10 is viewed from the same perspective with a common field-of-view "optical" axis. This configuration allows a two-dimensional map to be generated. For three-dimensional maps, a master camera and a master bio-field sensor can be co-located, perhaps in a single assembly. Secondary bio-field sensors 90, which enable triangulation of a detected object 45 (in FIG. 2, for example) in space, are offset positioned (with or without accompanying cameras) from the master sensor assembly.

To detect animate objects within an environment 10, the bio-electric field sensors must function to detect bio-fields from the living subjects 50 without requiring contact. One example of this type of emerging technology is described in U.S. Pat. No. 6,807,438, entitled "Electric Field Sensor", by R. Brun Del Re et al. That patent describes an electric potential sensor having one or more capacitive pick-up electrodes within a voltage divider network. The sensor can detect electrical potentials that occur in the human body via capacitive coupling (~1-40 pF), such as electro-cardiograms (ECGs), while an external housing provides shielding from ambient environmental EM fields. However, while this sensor is non-contact, it requires close proximity (<1 mm) to the subject to obtain useful signals.

Another example of a bio-electric field sensor in system 100 is the non-contact bio-electric field sensor 90, shown in FIG. 1 and disclosed in U.S. Patent Application Publication No. 2006/0058694, by T. D. Clark et al. The sensor 90 has a fixed sensor probe electrode 110 that capacitively couples to the body 60 under measurement at a distance (d). The sensor 90 includes a feedback, guard and input bias circuits 105 of the electrometer amplifier. In this circuit system 105, various feedback techniques that provide guarding, bootstrap and neutralization, have been applied to a low noise electrometer amplifier in order to increase its effective input impedance and reduce its input capacitance. The electro-dynamic bio-field sensor 90 measures a displacement current $i_d$ caused by an electric field 95, which is actually a rate of change of voltage measurement, with a high impedance circuit ($10^{15}\Omega$) and a low noise floor (~70 nV/Hz at 1 Hz). This optimized device conceptually acts as a perfect voltmeter that is able to measure very low, bioelectric potentials, including various bio-electric signals including ECGs and heartbeat signals (see, e.g., "Electric potential probes—new directions in the remote sensing of the human body", by C J Harland, T D Clark and R J Prance, published in Meas. Sci. Technol. 13, pp. 163-169, (2002)), EEGs and EOGs. In general, as the distance (d) between the subject (body 60) and the probe 110 decreases, the signal to noise improves dramatically, enhancing the potential diagnostic value. The Clark '694 reference also discloses that sensors 90 can be used individually, or in arrays for a variety of biological and non-biological purposes, including diagnostic or clinical monitoring of subjects.

As discussed in the Harland 2002 paper, this bio-sensing technology is capable of detecting bio-electric fields at relatively large distances (d) of at least 1 meter in a shielded room. More recently, as published in the paper "Biological and medical applications of a new electric field sensor", by R J. Prance, et al., Proc. ESA Annual Meeting on Electrostatics 2008, paper N2, cardiac signals were measured at a distance from the subject in an unshielded room, also occupied by operating computer equipment and other live electronics. As this technology improves further, bio-electric field sensing at distances of at least several meters between the sensors and subjects can be anticipated.

While the bio-electric field sensors 90 in system 100 can be considered passive devices that detect signals originating from animate objects 50 in the environment 10, a more active sensing approach can also be used. In particular, an optional electric field emitter 125 can emit calibrated known reference electrical fields that interact with objects (e.g., objects 40, 45, or 50 in FIG. 2) in the environment 10, thereby providing return signals, for example, differential electric fields, that can be indicative of an object's presence and location. These differential electric fields can be detected by the bio-field sensors 90 in the electric field sensing system 100.

FIG. 3 illustrates a method 300 for detecting animate objects 50 or inanimate objects 40, according to an embodiment of the present invention. In step 305, the data processing system 205 receives image data and electric-field data from the camera system 150 and the electric field sensing system 100 as previously discussed and as illustrated in an example by FIG. 4. In some embodiments, the image data and electric-field data (and any other data) received by the data processing system 205 is not directly received from the respective cameras or sensors in the peripheral system. In these embodiments, such data may be received from an intermediate device between the peripheral system 120 and the data processing system 205, not shown in FIG. 2. These intermediate devices may or may not process or manipulate such data. If these intermediate devices do process such data, it can be said that the processed data is derived from the respective cameras or sensors in the peripheral system.

The image data represents a captured image of the environment 10 or a portion thereof. The electric-field data represents electric fields present in the environment 10 or a portion thereof. Preferably, the electric-field data and the image data represent information gathered from an overlapping portion of the environment 10.

In step 310 of the method 300 FIG. 3, the data processing system 205 detects a candidate object, which is either an inanimate object (40a, 40b in FIG. 4, for example) or animate object (50a, 50b in FIG. 4) in the overlapping portion of the environment 10. Relative to image data, the image analysis programs 220 can use a variety of programs, such as eye detection or body shape detection to detect and locate candidate animate objects from the data for the imaged FOV 20. The image analysis programs 220 can also detect and locate candidate inanimate objects.

Figure 5:
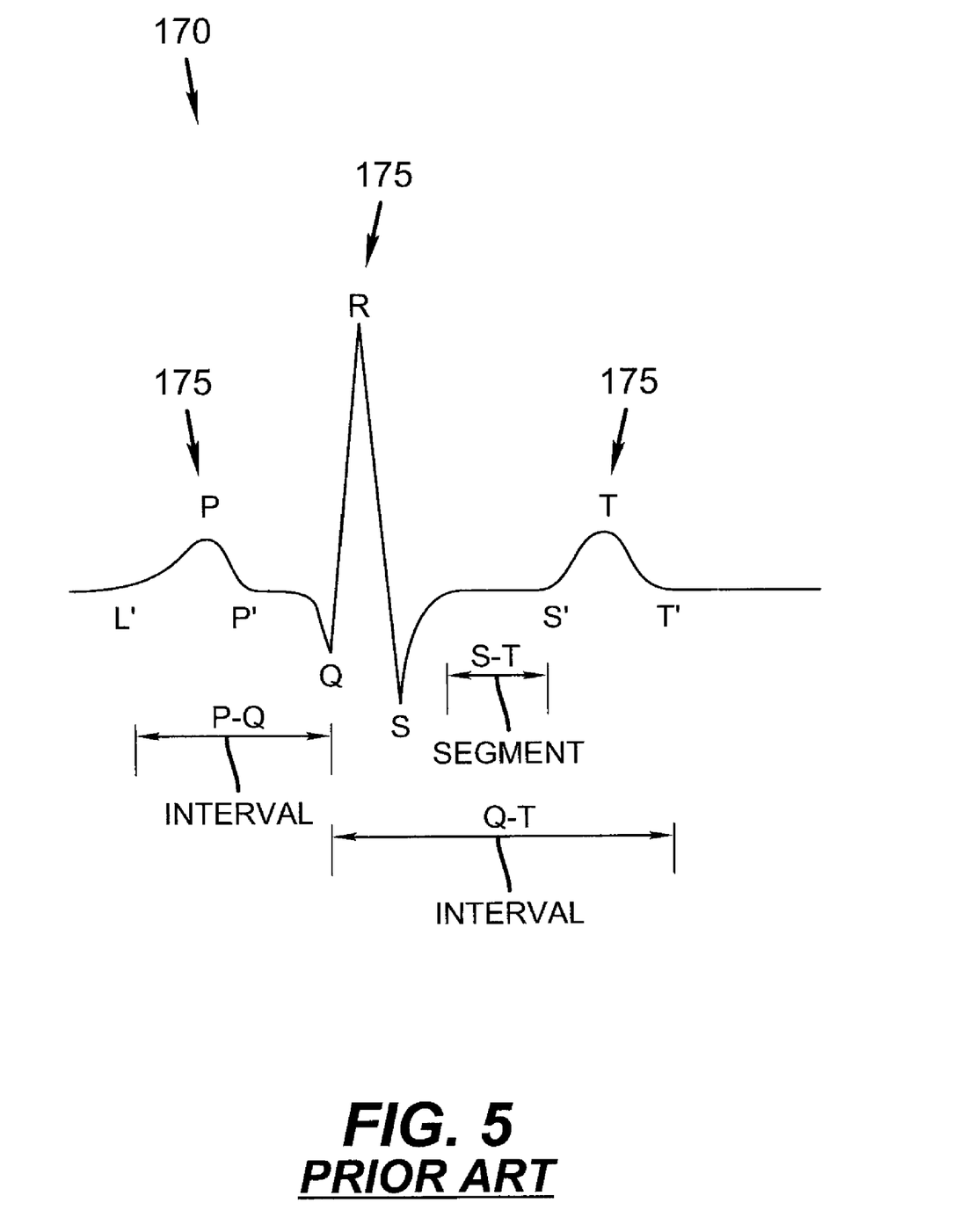
FIG. 5 illustrates an idealized ECG signal, as can be detected by a bio-electric field sensor.

Relative to electric-field data sensed by bio-field sensors 90, the bio-field signal interpretation programs 240 can detect and localize bio-field signals from the incoming electric-field data. Exemplary biometric signals, related to ECGs and heartbeats, are shown in FIG. 5, and will be discussed subsequently. Motion analysis by motion analysis program 230 can also contribute to detection of objects 45, including candidate animate objects 50 or candidate inanimate objects 40, aiding either the image analysis or bio-field interpretation approaches.

The data processing system 205 detects a candidate object at step 310 based at least upon an analysis of the image data, the electric-field data, or both, as received in step 305. Such analysis can include as an initial sub-step, preprocessing of the image data, the electric-field data, or both. For example, the image data can be subjected to image normalization (such as for sizing, brightness, contrast), color correction, or edge enhancement (sharpening), by image normalization programs 222. Such preprocessing can also include the building of a two-dimensional or three-dimensional map of the overlapping portion of the environment 10 captured by the camera system 150 and the electric field sensing system 100, as previously discussed. If a map is generated, the candidate object or objects detected at step 310 can be detected or located on such map. However, any technique for detecting objects 440, 45, or 50 from image data or electric-field data can be used at step 310.

For example, the data processing system 205 can process the image data using feature analysis programs 225, such as skin or hair detection programs, head, face, or eye detection programs, body shape or other object-shape detection programs, or texture-based programs. Programs that screen based on skin color or other color-evidenced features can be use if camera system 150 includes cameras with visible light spectral sensitivity. Infrared ("IR") based feature analysis programs can be used when the camera system 150 includes IR cameras. In addition to using feature analysis programs 225, the data processing system 205 can use motion analysis programs 230 to detect and localize candidate objects, as well as to track moving objects generally. While inanimate objects 40 can move, the chances that a moving object 45 is moving are high enough that motion detection can at least be an indicator for directing system resources to further efforts to classify an object. Additionally, motion data, such as that related to the movement of articulating limbs 62, is highly indicative of the presence of an animate object 50. Accordingly, it should be noted that the invention is not limited to any particular image processing technique used by the data processing system 205 to identify a candidate object in step 310. The same applies for steps 315 and 330, discussed below. A variety of image analysis techniques appropriate for the present invention are discussed subsequently.

In addition to or in lieu of preprocessing the image data, the data processing system 205 can preprocess the electric-field data in step 310 using the bio-electric field signal interpretation programs 240. Such programs can isolate bio-electric field data from other environmental data received at step 305. Bio-electric field signal interpretation programs 240 can also analyze the incoming electric-field data to detect a candidate object that is animate (e.g., 50a, 50b in FIG. 4). For example, electric fields associated with the heart beats of a living object 50 can be detected in the electric-field data by the data processing system 205 or in the electric-field sensing system 100, and used to detect candidate objects. These bio-electric field signal interpretation programs 240 can also combine data from multiple bio-electric field sensors in system 100 to triangulate or localize a candidate object within the environment 10. In the case that an optional electric field emitter 125 is used to provide reference fields, differential electric fields originating with the interaction of the reference electric field and a bio-electric field can be sensed by the multiple bio-field sensors in system 100 to detect and locate a candidate object. Under some circumstances, which are discussed subsequently, electric field sensing can also be used to detect and locate candidate objects (e.g., 40a, 40b in FIG. 4) that are inanimate. Accordingly, it should be noted that the invention is not limited to any particular electric-field data processing technique used by the data processing system 205 to detect a candidate object in step 310. The same applies for steps 315 and 330, discussed below.

In step 315 of the method 300 of FIG. 3, the data processing system 315 classifies the candidate object as animate or inanimate based at least upon an analysis of the image data, the electric-field data, or both. In this regard, when the data processing system 205 analyzes only the image data or the electric-field data to identify the candidate object, the data processing system 205 analyzes the other of the image data or the electric-field data used to identify the candidate object, or analyzes both the image data and the electric-field data. In other words, the data processing system 205 does not analyze only the image data or the electric-field data to both identify and classify the candidate object at steps 310 and 315, respectively. Upon conclusion of step 315, the data processing system 205 will have analyzed or compared both the image data and the electric-field data at some point in steps 310 and 315. Further in this regard, if the data processing system 205 analyzes both the image data and the electric-field data to identify a candidate object at step 310, the data processing system 205 classifies the candidate object as animate or inanimate at step 315 based at least upon an analysis of the image data, the electric-field data, or both the image data and the electric-field data.

By ensuring that both the image data and the electric-field data are analyzed by the data processing system 205 at some point in steps 310 and 315, false classifications of candidate objects in step 315 can be reduced as compared to conventional techniques. For example, a conventional technique that only analyzes image data may determine that a toy cat ("stuffed animal toy") is an animate object 50. In the present invention, however, the electric-field data will lack a bio-electric field signature associated with such object and, consequently, the data processing system 205 would classify the object as inanimate at step 315. For another example, a partially or completely hidden object, such as cat 50b hidden by chair 40a in FIG. 4, may be classified as inanimate, unclassifiable, or may not be detected at all by a conventional technique that analyzes image data only. However, the electric-field data, according to the present invention, can reveal the bio-electric field associated with a partially or completely hidden animate object in many circumstances. Consequently, such objects can be classified as animate in step 315 by the data processing system 205.

On the other hand, analyzing electric-field data only in steps 310 and 315 (and not image data) can limit the effectiveness by which a candidate object located in the monitored environment 10 is correctly detected and classified as animate. For example, the electric field sensing can be susceptible to noise, where signals from electronic devices mask bio-electric field signatures. Detection of bio-electric fields from an animate object 40 can also be prevented by intervening objects that are located between the object and the sensors 90, particularly if the objects are conducting (such as metallic). As a result, effectiveness of bio-electric field sensing in detecting and classifying candidate objects on its own can be limited. Accordingly, using a combined or dual sensing modality with both image data and electric-field data proves beneficial.

The data processing system 205 can use the bio-electric field signal interpretation program(s) 240, the image analysis program(s) 220, or both, to facilitate classification of a candidate object in step 315. In other words, many of the same programs 240, 220 used in step 310 to identify a candidate object are also used in step 315, but with the objective to classify the candidate object as animate or inanimate. As is discussed subsequently, classified objects can be classified further, as data detection and analysis permits. For example, an animate object 50 can be further classified as human or animal, or even as cat or dog for example. In this regard, although FIG. 3 shows steps 315 and 310 as separate and distinct steps, they can be considered a single step in some embodiments where both detection and classification occur concurrently or substantially concurrently. The same applies with optional step 330 with respect to steps 310, 315, or both. Obviously, if an object 45 leaves a monitored area before sensing and analysis is complete, then any ongoing object sensing and analysis for that object can be stopped.

If, at step 315 of method 300 of FIG. 3, an analysis of image data, electric-field data, or both yields an inconclusive result, the data processing system 205 can direct further sensing efforts by the electric field sensing system 100, the camera system 150, and any secondary sensors 160. Such further sensing efforts, represented by optional step 300, can continue until enough image data and electric-field data is available to classify the candidate object as animate or inanimate in step 315. Step 330 can also provide further classifications results, determining that an animate object 50 is a human, cat, or dog, for example. Potentially step 330 can also extend classifying to include identifying or recognizing an animate object 50 by associating detected biometric data with a known identity. In step 320, the data processing system 205 stores results of the classifying performed in step 315 (and optional step 330) in the processor-accessible memory system 215.

In optional step 335 of method 300 of FIG. 3, based upon results from the classifying step 315 (and optional step 330), the data processing system 205 can instruct a responsive device 270 to take action. Examples of such responsive devices include an electronic imaging apparatus (for example, an autonomous camera or an eye-safe projection system), an intruder alert system, or other specialty apparatus.

In some applications of the present invention, such as where safety is involved, it can be beneficial to use programs 220, 240 in steps 310 and 315 that operate quickly in real-time. For instance, if the responsive device 270 is a laser projector, the data processing system 205 may need to prevent the device 270 from projecting its lasers when a living object 50 is in the projection path of the device 270. In this regard, the data processing system 205 may need to quickly identify animate objects 50 in the projection path to avoid potential eye damage to the animate object.

Figure 4:
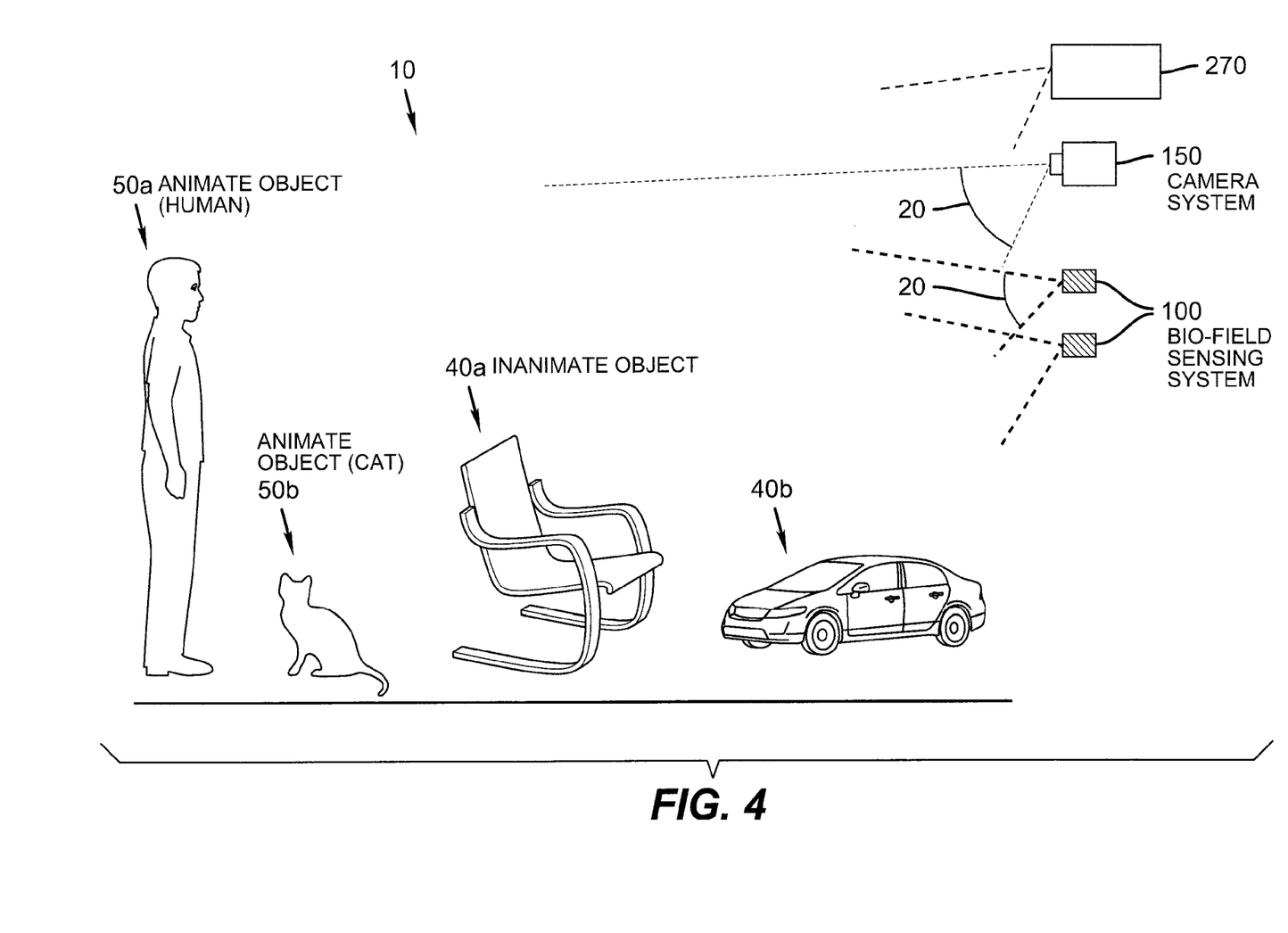
FIG. 4 illustrates an example of which the systems and methods of FIGS. 2 and 3 are executed, according to an embodiment of the present invention.

Thus far, functional aspects of the present invention have been described relative to FIGS. 2-4. The system 200 and method 300 are dependent not only on the functionality of the camera system 150 and the bio-field sensing system 150, but also on the image analysis programs 220 and bio-field signal interpretation programs 240, the latter of which merits further description.

Bio-field signal interpretation, as performed by programs 240, is dependent on the signals picked up by the bio-electric field sensors (90, e.g.) in the bio-electric field sensing system 100. For example, a normal heartbeat is initiated by a small pulse of electric current. This tiny electric "shock" or wave spreads rapidly in the heart and makes the heart muscle contract in a cyclic fashion, pumping blood through the 4 chambers of the heart. Time interval data (P-Q, S-T, Q-T) from an ECG curve (FIG. 5) can be used to determine whether the electrical activity is normal or slow, fast or irregular, while magnitude data can indicate whether parts of the heart are too large or are overworked. While the present invention does not have to target diagnostic interpretation, some aspects of heart beat activity information associated with a candidate object and present in electric-field data, such as heart beat frequency, pulse shape, timing, or combinations thereof, can be useful. Such heart beat activity information can, but does not have to be, derived from an ECG. As elaborated upon below, such heart beat activity information can be useful for, among other things, detecting candidate objects, classifying candidate objects as animate or inanimate, further classifying types of candidate objects, or combinations thereof.

Basically, an electrocardiogram (ECG or EKG) is a recording of the electrical activity of the heart over time. FIG. 5 depicts a model of a typical ECG signal 170, with the standard ECG signal features 175, including the P wave, the QRS complex, and a T wave shown. The right and left atria or upper chambers make the first wave called a "P wave", following a flat line when the electrical impulse goes to the bottom chambers. The right and left bottom chambers or ventricles make the next wave called a "QRS complex." The final wave or "T wave" represents electrical recovery or return to a resting state for the ventricles. Standard ECGs are typically measured using data collected from various locations in the circulatory system, such as the limbs and the heart. In this regard, sensor 90 or other bio-electric field sensors, may, in some configurations, measure heart beat or ECG-type signals from the torso or other locations in the circulatory system besides the heart.

While embodiments of the present invention target non-clinical purposes and signal interpretation, interpretation of an ECG signal 170 by bio-electric field analysis programs 240 can be used to distinguish humans (animate object 50a) from animals (animate object 50b). In particular, humans and animals exhibit different pulse shapes and timings in their ECGs or heart beat pulse profiles. For example, the paper "Non-drug-related electrocardiographic features in animal models in safety pharmacology", by R. L. Hamlin, published in the Journal of Pharmacological and Toxicological Methods, Vol. 52, pp. 60-76, 2005, discusses aspects of cross-species comparative electro-cardiology. As one example, the ECG patterns of carnivores (including dogs, cats, primates, and man) have different QRS complexes (see FIG. 5) than those of other animals (typically herbivores such as horses, goats, and pigs), due to differences in the distribution of Purkinje fibers (specialized myocardial muscle fibers) that conduct electrical impulses within the ventricles. As another example, dogs exhibit greater variability in the P-wave and the S-T/T portion (or complex) of the ECG signal 170 than is present in humans. If such differences, using heartbeat data or ECGs measured at a distance (d) in meters, are of sufficient magnitude and distinction, then signals for animals and people can be distinguished from each other for purposes of step 330.

However, if an accurate ECG signal cannot be obtained at a distance (d), detection of heartbeat or arterial pulse signals, rather than the more detailed ECG waveforms, can be sufficient. In this regard, heartbeat frequency can be used to distinguish humans from animals or particular types of animals at step 330. (Of course, if ECG signals can be obtained, heartbeat frequency can also be used in that case.) The human heartbeat frequency at a normal activity level is at ~60-80 beats per minute ("bpm") for adults, and 100-130 bpm for children. By comparison, dogs' resting heartbeat rates are faster than adult humans, depending on size (small at 100 bpm, to large at 75 bpm), while domestic cats and birds are faster yet (150 and ~400 beats/min respectively), and reptile rates are slower (35-45 bpm). In general, large creatures have slower heart rates, as more time is required to clear the heart's volume of blood. While heartbeat frequencies increase significantly with activity level (170-220 beats/min for humans, 270 beats/min for dogs, and 1000 beats/min for small birds flying), typically the area of living beings physical activity likewise also increases. Thus, when using multiple bioelectric sensors 90, heartbeat rates can be correlated with a detected range or area of associated motion, using motion analysis program 230, to aid classification of an animate being 50 as a human or animal, or dog or cat. Potentially, a set of multiple heartbeat measurements from multiple offset bio-field sensors 90 can be mapped over a single contiguous body 60, and compared to a library of characteristic body shape templates, to aid object characterization.

In some embodiments, classifications of a candidate object as human or animal (or even particular type of animal) can be performed based on detection and analysis of other bio-electric field signatures detected by the electric field sensing system 100. For example, electro-encephalogram ("EEG") or electro-oculograms ("EOG") signals can be used. Electro-encephalograms depict electrical activity in the brain, and for example can be used to measure the α and β rhythms that are associated with eye function (open or closed respectively) or brain activity associated with epilepsy, sleep disorders, brain tumors, and other health conditions. Electro-oculograms (EOGs) measure electrical activity associated with eye movement, and correlate with left-right and up-down eye movements. However, in general EEG and EOG signals are much weaker than ECG signals, and are thus less likely to be used as detection means for the present invention. In summary, the ECGs (or heartbeats), EEGs and EOGs, or their remotely measured bio-electric field analogues or equivalents, are examples of measurable biological characteristics or biometrics of animate-being activity that can be detected and used for the present invention.

With respect to the image-based approach, enabled by camera system 150 and image analysis programs 220, there are a wide variety of techniques that can be used. Exemplary approaches include screening for animate objects 50 using IR imaging, body shape analysis, motion analysis, person-in-box analysis, head and face detection analysis, or combinations thereof.

As a first example, IR images can be helpful because they are readily distinguished from any displayed (for example, projected) image content. IR imaging can be used both for body-shape and facial feature imaging. However, it is important to note that the appearance of humans and animals changes when viewed in near-IR (NIR) light. For example, key human facial features (hair, skin, and eyes, for example) look different (darker or lighter, etc.) than in real life depending on the wavelength band. As an example, in the NIR below 1.4 mm, skin is minimally absorbing, and both transmits and reflects light well, and will tend to look bright compared to other features. The surface texture of the skin images is reduced, giving the skin a porcelain-like quality of appearance. Whereas, above 1.4 mm, skin is highly absorbing and will tend to look dark compared to other features. As another example, some eyes photograph very well in infrared light, while others can be quite haunting. Deep blue eyes, like deep blue skies, tend to be very dark, or even black. Thus, these imaging differences can aid or confuse body feature detection efforts.

A paper by Dowdall et al., "Face detection in the near-IR spectrum", published in the SPIE Proc., Vol. 5074, pp. 745- (2003) describes a face detection system which uses two IR cameras and lower (0.8-1.4 μm) and upper (1.4-2.4 μm) IR bands. Their system employs a skin detection program to localize the image analysis, followed by a feature-based face detection program keyed on eyebrows and eyes. While Dowdall et al. provides insights regarding imaging and image analysis of people and body features, this paper does not consider IR imaging of pets, such as cats and dogs, for whom the image differences with IR imaging, will be different. Moreover, depending on what the people or animals are doing, or what clothes they are wearing, IR image interpretation may be confused. Finally, the Dowdall approach requires two IR cameras and filtering, and likely at least two a light sources 212 to illuminate the local environment 10. Thus, IR-based facial feature detection, used by itself, can be insufficient for the purposes of the present invention.

In summary, IR imaging can potentially provide valuable data from which the data processing system 205 can localize and size an object 45 in step 310. IR imaging can also be readily used to outline a body shape to determine a silhouetted profile of the object, from which a body shape can be determined. However, the potential confusion of image interpretation, particularly related to body pose or partial obscuration, means that IR imaging cannot always reliably distinguish animate objects 50 as a subset of objects 45 in a local environment 10.

Figure 6A:
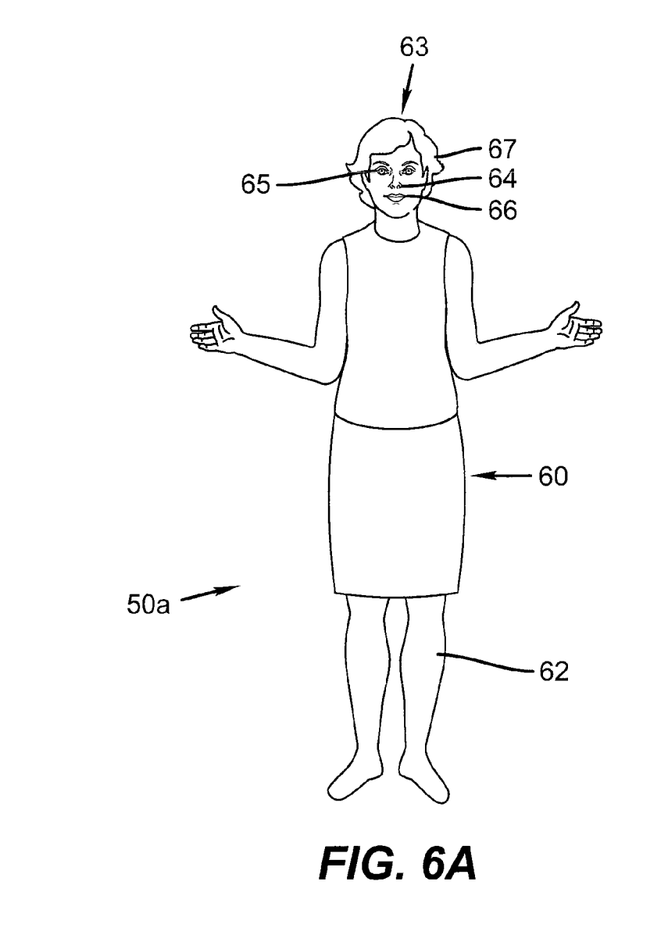
FIG. 6a illustrates a subject or a person who can be detected as an animate object, and salient features thereof.
Figure 6B:
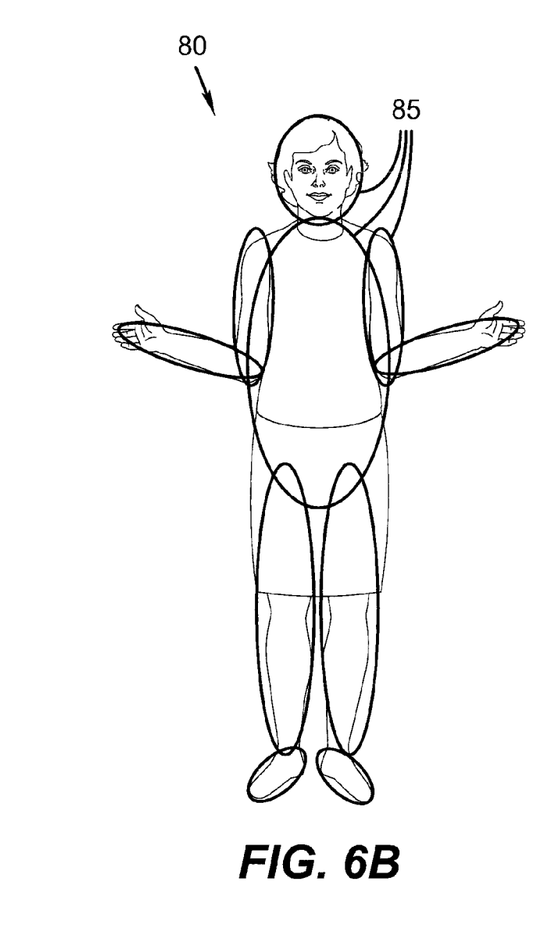
FIG. 6b illustrates an ellipsoid human body model.

As another exemplary approach, the feature analysis program 225 can apply body shape detection programs, using body models known in the art, to quickly detect people or animals. Body models can be understood using the illustrations of FIGS. 6a and 6b. FIG. 6a depicts a human 50a who has a physical body 60 including various limbs 62, a torso, and a head 63 with hair 67, with a face 64 having eyes 65, mouth 66, and nose. FIG. 6b then illustrates a simplified body model 80 in which the torso, limbs, and head are represented by a series of interconnecting body shape ellipses 85. Body shape detection or shape detection programs more generally can then be used to classify candidate objects as animate or inanimate and, if animate, potentially animate people or animals.

In particular, D. Forsyth et al, in the paper "Finding People and Animals by Guided Assembly", (published in the Conference on Image Processing, pp. 5-8, vol. 3, 1997) describes a method for finding people and animals based on body plans or grouping rules for using basic geometric shapes (cylinders) to identify articulating forms. Body images are segmented into a series of interacting geometrical shapes, and the arrangement of these shapes can be correlated with known body plans. Body shape analysis can be augmented by analyzing the movement characteristics, frequency, and direction of the various articulating limbs, to compare to expected types of motion, so as to distinguish heads from other limbs. Such body model data that includes movement characteristics can be used by motion analysis program 230 in detecting and classifying animate objects 50.

Certainly, body shape modeling can be very useful for quickly determining that an object 100 in detecting an object (step 310), and then in classifying an object as animate or inanimate (steps 315 and 330). The performance (accuracy and speed) of image search based on body shape models is of course reduced on a situational basis. For example, observed animate bodies can be arranged in shapes which are complex and non-obvious, or can be further obscured by clothing, hair, or fur. Moreover, under the right circumstances, some body shapes can be confused. For example, a small dog might be classified as a cat. Given these various complications, body-shape-based detection programs, by themselves, can be insufficient for the purposes of the present invention.

As another image-based approach, images can be screened to locate people or animals directly without first finding body shapes. In particular, the paper, "Putting Objects in Perspective", D. Hoeim et al., published in the IEEE Proc. on Computer Vision and Pattern Recognition (CVPR) 2006, pp. 2137-2144, describes an approach for person detection which is based on knowledge or estimation of the camera viewpoint and estimation of the rough surface geometry in the scene to define the probability of locating a person in a given image location. Once such a program has examined the surrounding context to localize the candidate areas ("person in box") that a person is likely to be in, after which, a person detection program can be run to confirm the person detection. While this technique was developed to quickly screen for pedestrians and cars in complicated street view images, the reduced range of geometrical variation in a local environment 10, such as a room, would likely aid this program. This kind of technique can be used to quickly assess the sensed images to localize likely animate object locations, and then other techniques, such as body shape model analysis (discussed above) or direct head or facial feature screening analysis (discussed below) can also be used.

In addition to screening with IR images, or by body shape models or person-in-box criteria, it is useful to search images by looking for salient characteristics such as heads, faces, or eyes. As one example, images can be analyzed to look directly for nominally circular skin-toned areas. A program can analyze for color data that is common to skin tones for all ethnic groups, thereby reducing statistical confusion from racial, ethnic, or behavioral factors. As an example, the paper "Developing a predictive model of human skin colouring", by S. D. Cotton (published in the SPIE Proc., Vol 2708, pages 814-825, 1996) describes a skin color model that is racially and ethnically insensitive. For example, this technique can be used to localize or confirm heads 63 or faces 64 in image areas previously assessed by body shape or person-in-box methods. While this analytical technique can be fast, directional variations in head pose, including poses dominated by hair 67, can complicate the analysis. Additionally, this technique does not help with animals.

As another example, an image analysis program 220 of the data processing system 205 can apply texture-based methods at step 315. One example is detection of hair 67, such as described in "Detection and Analysis of Hair," by Y. Yacoob and L. David, which was published in IEEE Trans. on PAMI, Vol. 28, pp. 1164-1169, 2006. For embodiments of the present invention, which require detection rather than recognition, a program of this type can presumably be simplified and operable with IR images, as well as visible light images. Significantly, this type of program can be adapted to assist in the detection of animal fur, and may have value in tracking fur color patterns. However, texture based models, which key typically on features with high spatial frequency and variable contrast differences, are usually slow programs. Notably however, the system 200 can use reference image data for a household pet, or simply see the pet on an ongoing basis, and then a model or templates can be developed to enable rapid searching for that pet.

As another alternative to screening or confirming heads 63, templates or models of head and face geometry can be used. For example, an Active Shape Model (ASM), as described in "Active Shape Models—Their Training and Application", by T. F. Cootes, C. J. Taylor, D. Cooper, and J. Graham, published in Computer Vision and Image Understanding 61, pp. 38-59, January 1995, can be used. Facial models key on facial features described by face points, vectors, or templates. Simplified facial models that support fast face detection programs are appropriate for embodiments of the present invention. In practice, many facial detection programs can search quickly for prominent facial features, such as eyes, nose, and mouth, without necessarily relying on body localization searches first. However, these programs are then prone to false positives, identifying clocks or portions of textured wall surfaces as having the sought facial features. Also most facial detection or recognition models, except the 3D composite models, are 2D models that function well in examining frontal (or direct-on) facial images, but which fail at increasing rates as the head pose becomes more and more of a side view. As a result, a related search approach, based on head shape templates can be used to locate and track heads 63. The head shape templates comprise sets of head and facial outlines for different poses, in which features such as the chin, mouth and lips, nose, eyes, forehead, ears, or hairline become detection attributes. However, while this is a plausible search approach for humans, the range of pose variations with animals can reduce the value of head shape templates in analyzing their sensed images.

As yet another image-based approach, eye detection can be used. Typically, eye detection is poor way to search an entire image to reliably locate animate objects 50. However, when it is used in combination other feature analysis techniques 225 (e.g., body, hair, head, face detection), it can be another way to quickly classify a candidate object as animate or potentially animate at step 315 or to further classify the candidate object at step 330. For example, instead of searching the entire set of image data received at step 305 for eyes, already-detected head or face regions within a candidate object can be searched for eyes. Detecting eyes after detecting a head or face can increase the confidence with which a candidate object is classified as animate. Some programs, known in the art, can perform image search tasks for eye features using eye-specific deformable templates, such as suggested in the paper "Feature extraction from faces using deformable templates", by A. L. Yuille, P. W. Hallinan, and David S. Cohen, published in International Journal of Computer Vision, Vol. 8, pp. 99-111, 1992. The deformable templates can describe the generalized size, shape, and spacing of the eyes. Templates can also look for expected shape combinations and geometries associated with the eyes and mouth, the eyes and nose, or the eyes and eyebrows.

There is a particular circumstance where search of incoming image data for eyes can be quick at directly detecting and locating animate objects 50. In particular, it can be useful to search for eye-shine, which is associated with common nocturnally-advantaged animals, such as dogs and cats. Compared to humans, canine or feline pet-eyes have superior low light vision because of an internal highly reflective membrane layer in the back of the eye, called the "tapetum lucidum". It acts to retro-reflect light from the back of the retina, giving the animal an additional opportunity to absorb and see that light, but also creating eye-shine, where the eyes to appear to glow. This effect similar to the red-eye effect in humans, but with a greater color range. Animal eye-shine is also more frequently perceived than the photographic-flash-enabled red-eye effect in humans, but it also is an angularly sensitive effect (only detectable within ~15 degrees of eye normal). While eye-shine is angularly sensitive, due to the high brightness or high contrast of the eye-shine eyes relative to the surround, it can be easier and quicker to find eyes exhibiting eye-shine than to search for the heads 63, or bodies 60, of the animals 50b first.

As can be gleaned from the immediately preceding descriptions, relying on image data in steps 310, 315, and 300 alone can result in inconclusive classification results. E.g., is the detected object 45 an animate object or a picture of a person (inanimate)? Accordingly, it can be beneficial to use multiple imaging analysis techniques in combination to improve the accuracy of the results. However, even using multiple image analysis techniques, false positives can still occur. For example, problematic inanimate objects that can lead to false positives when using only image analysis techniques can include analog clock faces, stuffed animals or manikins. Problematic animate objects that can lead to false negatives include when people 50a or animals 50b are positioned in difficult poses, or are at least partially obstructed or shielded from the camera view. In some cases, object movement and tracking thereof by motion analysis program 230 can help. However, combining multiple image-based feature analysis techniques is typically time consuming.

Accordingly, the data processing system 205 also analyzes electric-field data from the electric field sensing system 100 in steps 310 or 315. For example, if an analysis of image data results in the detection of a human face, an analysis of the electric-field data could determine whether or not a bio-electric field is associated with that face. If so, the data processing system 205 can determine that the human face (i.e., the candidate object) is animate at steps 315 or 300. If not, the data processing system can determine that the human face is inanimate. Or, if an analysis of image data at step 310 detects a partially obscured candidate object (e.g., a body of a cat 50b in FIG. 4), and an analysis of the image data at step 315 is unable to classify the candidate object (e.g., because the data processing system 205 does not know with high accuracy that the object is a cat from the limited data), then an analysis of the electric-field data can reveal a bio-electric field associated with the object. Such bio-electric field could be used by the data processing system 205 to classify the object as animate. As another example, image data analysis of a partially occluded animate object 50 may provide an initial classification such as "animate/uncertain" or "animate/hidden" while occluding objects in front of the target object prevent bio-field sensing from acquiring sufficient signal. Image data analysis can have an advantage over electric-field data analysis when identifying candidate objects and their outlines in step 310 and when classifying types of objects at step 330, discussed below. However, a largely occluded, silent, and stationary animate object, will likely be undetected by imaging techniques alone, for at least some time period.

The two sensing modalities work in complimentary ways. The bio-electric field sensing modality will quickly and directly locate living objects 50 with a low risk of false positives, while mostly ignoring surrounding inanimate objects 40. Bio-electric field sensing can provide positive readings, or indeterminate readings when signal clarity is insufficient. There are also circumstances, particularly when an animate object 50 is significantly occluded (for example, by a large conducting object 45 or another animate object 50) or the ambient electric field noise is high or the distance (d) is large, in which the probabilities of an indeterminate, uncertain, or false negative result from bio-field sensing will increase. However, the probabilities for false positive results in detecting animate objects 50 with bio-electric field sensing are comparatively lower than with imaging, although they can occur. Whereas, the imaging modality is better at detecting and locating most or all objects, whether animate or inanimate, as well as determining size, shape, continuity and other object characteristics. While there are circumstances where hidden or occluded objects can be invisible to both modalities, in general, the two approaches are compensatory, and correct animate object classification can occur more accurately and quickly as a result.

Object detection (step 310) and object classification (step 315) can yield inconclusive results, particularly if objects are hidden. Interim classifications (such as partially hidden or indeterminate) can be assigned while further detection and analysis occurs (step 330). In some embodiments, the classification performed in steps 315 and 330 of the method 300 of FIG. 3 can be accompanied by a confidence value 250 or score indicative of the degree of confidence that the data processing system 205 has in its classification result. Confidence values are measures of the confidence assigned to the value of an attribute, and which are often expressed as a percentage (0-100%) or a probability (0-1). Confidence values can be calculated to indicate the likelihood or probability that an object in a given monitored area of a local environment 10 matches a classification. Basically confidence values enable the data processing system 205 to assess the risk that a classification result is a true or false positive or a true or false negative. For example, high confidence values (for example >75%) can indicate that the data processing system 205 has determined an object classification (such as animate or inanimate) with high probability or certainty. Low confidence values (for example <25%) can indicate that data processing system 205 has determined an object classification (such as animate or inanimate) with a low degree of confidence (high uncertainty) that the answer is correct, or that no classification should yet be proposed. Intermediate values, for example, can mean that the confidence is high that at least one animate object has been detected, but that partial or total occlusion of that object (it is hidden) reduces the certainty. Intermediate results can also occur when one sensing modality (bio-field sensing, for example) indicates an object classification (animate, for example) for a given object, while another sensing modality (imaging) indicated the opposite object classification (inanimate) for the same object. In this example, uncertain results (<75%) can lead to further monitoring.

Confidence values 250 can be evaluated individually for each sensing modality (image/electric field), or in combination. The imaging modality analysis can also include multiple confidence values for the different analysis approaches (such as body shape or IR imaging). Of course, the definitions of high, intermediate, and low confidence can be defined by the needs of a given application.

Confidence values 250 can be calculated by the data processing system 205, based upon its analysis of image data, electric-field data, or both, as well as other sensed data, as appropriate. In general, either bio-electric field sensing or image capture and analysis can lead to a positive (high confidence) result in identifying an object as animate, or a false positive, or a false negative, as well as indeterminate results for identifying animate objects. Imaging intrinsically provides more awareness of the presence of objects, whether animate or inanimate in an environment 10 than does bio-field sensing. This can be both advantageous and disadvantageous. On the one hand, this means the number of objects to be assessed can increase, but on the other hand, the probabilities of locating all animate objects within the environment 10 also increases. By comparison, bio-electric field sensing intrinsically senses animate objects 50 rather than inanimate objects 40. While detection of inanimate objects 40 by bio-electric field sensors in sensing system 100 can occur, the straightforward reliable detection of animate objects 50 while generally ignoring inanimate objects 40 can speed system function.

In step 330, which is optional, the data processing system 205 can further classify the candidate object beyond merely classifying it as animate or inanimate. Such further classification can occur using the image analysis programs 220 and bio-electric field signal interpretation programs 240 described above. For example, if a human body shape detection program is used in step 310 to identify a candidate object, and electric-field data is used to confirm that the candidate object is a living (animate) object in step 315, it follows that the data processing system could further classify the animate object as human. Other further classifications could indicate that the candidate object is animal, partially hidden (if an analysis of the image data indicates so), or moving, as can be determined by the motion analysis programs 230. In the case of animals, particular types of animals could be identified at step 330. Any new or altered classifications provided in step 300 can also be qualified with a calculation of associated confidence values 250.

With respect to the present invention, emphasis has been placed on detecting animate objects from a local environment 10, where numerous inanimate objects may be present. The image based approach, using analysis programs 230 can also use templates, motion, or other visual cues to detect a candidate object and then classify it as an inanimate object 40. That is rather, inanimate objects can be classified as such by direct means, rather than by exclusion as not-animate (non-living).

As a related aspect, it has been noted that bio-field sensing intrinsically senses animate objects 50 rather than inanimate objects 40. However, passive bio-field sensors 90, such as the prior art sensors of FIG. 1, can detect at least some moving inanimate objects 40 by sensing spatio-temporal changes in the ambient electric fields caused by the motion of the objects. These ambient electric fields can be detected by either the bio-field sensors 90, or by secondary electric field sensors (160) that are not specifically optimized for bio-electric field sensing. Alternately, if system 200 includes an optional reference electric field emitter 125 in addition to multiple bio-electric field sensors 90, then at least some stationary inanimate objects 40 can be sensed, for example by detecting and locating differential electric fields in the field pattern. (In this regard, secondary electric field sensors 160 and reference electric field emitter 125 can be considered part of the electric-field sensing system 100 in some embodiments, even though they are shown separately in FIG. 2.) Essentially, the presence of inanimate objects 40 can be detected or inferred indirectly, by mapping areas in 2D or 3D space that have reduced or blocked electric field transmissivity or reflectivity. In general, it can be expected that bio-field sensors 90 will more readily detect moving or conductive inanimate objects 40, rather than stationary or non-conducting inanimate objects 40. Some localized electric field noise sources (such as electronic devices) can also be detected by sensing their emitted EM fields. Secondary electric field sensors 160, tuned for sensitivity to common electronic devices or ambient electric field spectra, can be used for this purpose.

It is noted that other types of secondary sensors 160, such as light levels or optical spectrum sensors can be used by system 200, for example to enable analysis of ambient illumination conditions. This data can be used from image normalization (222). Secondary sensors 160 can also include microphones, whether individual, multiple, or directional. System 200 can then use audio data analysis as well in detecting and classifying objects. Ultrasound or microwave sensing for animate objects are other examples.

It is to be understood that the exemplary embodiments are merely illustrative of the present invention and that many variations of the above-described embodiments can be devised by one skilled in the art without departing from the scope of the invention. It is therefore intended that all such variations be included within the scope of the following claims and their equivalents.

PARTS LIST d air gap
10 Environment
20 Field of view (FOV)
40, 40*a*, 40*b* Inanimate object
45 Object
50 Animate object
50*a* Animate object—human
50*b* Animate object—animal
60 Body
62 limbs
63 head
64 face
65 eyes
66 mouth
67 hair
80 body model
85 body shape ellipses
90 Bio-electric field sensor
95 Electric field
100 Electric field sensing system
105 Circuit
110 Probe electrode
115 Housing
120 Peripheral System
125 Reference electric field emitter
130 User Interface System
150 Camera system
160 Secondary sensor
170 ECG signal
175 ECG signal features
200 System
205 Data Processing System
212 light source
215 Processor-Accessible Memory System
220 Image analysis program(s)
222 Image normalization program(s)
225 Feature analysis program(s)
230 Motion analysis program(s)
240 Bio-electric field analysis program(s)
245 Environmental data interpretation program(s)
250 Confidence values
270 Responsive device
300 Method
305 Step
310 Step
315 Step
320 Step
330 Step
335 Step

The invention claimed is:

1. A method implemented at least in part by a data processing system, the method for detecting objects in an environment, and the method comprising:
receiving image data representing a captured image of the environment or a portion thereof;
receiving electric-field data from or derived from a bio-electric field sensing system including non-contact bio-electric field sensors, the electric-field data including bio-electric-field data sensed from bio-electric fields present in the environment or a portion thereof, and the electric-field data and the image data representing information gathered from an overlapping portion of the environment;
detecting a candidate object in the overlapping portion of the environment and classifying the candidate object as animate or inanimate, based at least upon an analysis of the image data and the electric-field data, wherein the analysis of the electric-field data includes an evaluation of whether the electric-field data includes at least a bio-electric field; and
storing information pertaining to results of the classifying in a processor-accessible memory system.

2. The method of claim 1, wherein the detecting, the classifying, or both comprise analyzing the image data using at least body shape detection, head detection, skin area detection, face detection, eye detection, motion analysis, or combinations thereof.

3. The method of claim 2, wherein the detecting, the classifying, or both comprise analyzing the image data using eye detection, and the eye detection includes the use of eye-specific deformable templates or pet-eye detection.

4. The method of claim 1, wherein if the candidate object is classified as animate, the method further comprises classifying the candidate object as human or animal.

5. The method of claim 4, wherein if the candidate object is classified as animal, the method further comprises classifying the candidate object as a particular type of animal.

6. The method of claim 1, wherein the bio-electric-field data includes heart beat activity information associated with the candidate object.

7. The method of claim 6, wherein if the candidate object is classified as animate, the method further comprises classifying the candidate object as human or animal based at least upon an analysis of the heart beat activity information.

8. The method of claim 6, wherein the heart beat activity information includes heart beat frequency, pulse shape, or timing, and the analysis of the heart beat activity information includes an analysis of the heart beat frequency, pulse shape, or timing.

9. The method of claim 1, wherein the electric-field data includes electro-encephalogram (EEG) information or electro-oculogram (EOG) information associated with the candidate object.

10. The method of claim 1, wherein the classifying includes an analysis of both the image data and the electric-field data.

11. The method of claim 1, wherein the classifying further classifies the candidate object as hidden based at least upon an analysis of the image data or the electric-field data.

12. The method of claim 1, wherein the candidate object is classified as inanimate based at least upon an analysis of the electric-field data.

13. The method of claim 1, wherein the electric-field data includes ambient electric field information representing ambient electric fields present in the environment, wherein the classifying classifies the candidate object as an inanimate moving object based at least upon an analysis of spatio-temporal changes in electric fields derived at least in part from the ambient electric field information.

14. The method of claim 1, wherein the classifying classifies the candidate object as inanimate based at least upon a detecting of differential electric fields represented in the electric-field data.

15. The method of claim 1, wherein the classifying of the candidate object includes calculation of confidence values based upon the received data from either image capture or bio-electric field sensing that indicates a probability that the candidate object correctly matches a determined classification.

16. The method of claim 1, wherein if the classifying of an object as animate or inanimate is indeterminate or indicative of an uncertain classification based upon the received data from either image capture or bio-electric field sensing, then continued detecting and classifying activities related to that object occurs using received data from at least the other of either image capture or bio-electric field sensing that was not previously used.

17. The method of claim 1, further comprising instructing a responsive device to take action based at least upon the results.

18. A method for detecting objects in a local environment comprising:
   operating at least one camera to acquire images and associated image data of the local environment and objects therein;
   detecting and locating candidate objects in the local environment based at least upon an analysis of the image data;
   operating at least one non-contact bio-electric field sensor to acquire electric-field data including bio-electric-field data from at least one source of bio-electric fields that are present within the local environment;
   detecting and locating candidate objects in the local environment based at least upon an analysis of the acquired bio-electric-field data; and
   classifying at least one of the candidate objects as animate or inanimate at least by comparing the acquired bio-electric-field data and the image data.

19. The method of claim 18, wherein the bio-electric-field data is indicative of heart-beat or circulatory activity, brain activity, or eye activity.

20. The method of claim 18, wherein the analysis of the image data includes body shape detection, head detection, skin area detection, face detection, eye detection, motion analysis, or combinations thereof.

21. The method of claim 18, wherein the classifying classifies the candidate object as inanimate (a) based at least upon a detecting of differential electric fields represented in the electric-field data, or (b) detecting spatio-temporal changes in electric fields based upon an analysis of the electric-field data.

22. A processor-accessible memory system storing instructions configured to cause a data processing system to implement a method for detecting objects in an environment, wherein the instructions comprise:
   instructions for receiving image data representing a captured image of the environment or a portion thereof;
   instructions for receiving electric-field data from or derived from a bio-electric field sensing system using non-contact bio-electric field sensors, the electric-field data including bio-electric-field data sensed from bio-electric fields present in the environment or a portion thereof, and the electric-field data and the image data representing information gathered from an overlapping portion of the environment;
   instructions for detecting a candidate object in the overlapping portion of the environment and classifying the candidate object as animate or inanimate, based at least upon an analysis of the image data and the received electric-field data, wherein the analysis of the electric-field data includes an evaluation of whether the electric-field data includes at least a bio-electric field; and
   instructions for storing information pertaining to results of the classifying in a processor-accessible memory system.

23. A system comprising:
   a data processing system;
   a camera system communicatively connected to the data processing system;
   an electric-field-sensing system that senses electric fields including bio-electric fields using non-contact bio-electric field sensors, the sensing system communicatively connected to the data processing system; and
   a memory system communicatively connected to the data processing system and storing instructions configured to cause the data processing system to implement a method for identifying objects in an environment, wherein the instructions comprise:
   instructions for receiving, from the camera system, image data representing a captured image of the environment or a portion thereof;
   instructions for receiving, from the electric-field-sensing system, electric-field data including bio-electric-field data sensed from bio-electric fields present in the environment or a portion thereof, the electric-field data and the image data representing information gathered from an overlapping portion of the environment;
   instructions for detecting a candidate object in the overlapping portion of the environment and classifying the candidate object as animate or inanimate based at least upon an analysis of the image data and the electric-field data, wherein the analysis of the electric-field data includes an evaluation of whether the electric-field data includes at least a bio-electric field; and instructions for storing information pertaining to results of the classifying in the processor-accessible memory system.

24. The system of claim 23, wherein the non-contact bio-electric field sensors are electrical potential probes that measure displacement currents caused by the bio-electric fields.

25. The system of claim 23, further comprising an electric field emission system communicatively connected to the data processing system, the electric field emission system including one or more electric field emitters that emit known electric fields into the environment, the emitted electric fields interacting with objects in the environment and providing return electrical fields sensed by the electric-field-sensing system.

26. The system of claim 23, further comprising secondary sensors communicatively connected to the data processing system, wherein the instructions further comprise instructions for receiving secondary sensing data from the secondary sensors, the secondary sensor data representing audio information, microwave information, ultrasound information, other electric field information, or combinations thereof, present in the environment, and wherein the instructions for detecting and classifying include instructions for analyzing the secondary sensing data.

27. The system of claim 23, further comprising a responsive device communicatively connected to the data processing system, wherein the instructions further comprise instructions for causing the responsive device to take action based at least upon the results of the classifying.

* * * * *